United States Patent [19]

VandenBerg

[11] Patent Number: Plant 6,802

[45] Date of Patent: May 16, 1989

[54] CHRYSANTHEMUM PLANT NAMED POMONA

[75] Inventor: Cornelis P. VandenBerg, Salinas, Calif.

[73] Assignee: Yoder Brothers, Inc., Barberton, Ohio

[21] Appl. No.: 135,298

[22] Filed: Dec. 21, 1987

[51] Int. Cl.[4] ..... A01H 5/00

[52] U.S. Cl. ..... Plt./80

[58] Field of Search ..... Plt./76, 80

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Pomona particularly characterized by its flat capitulum form; decorative capitulum type; red-purple to purple ray floret color; diameter across face of capitulum of up to 13.5 cm at maturity when grown as a pinched disbudded pot mum; uniform nine week photoperiodic flowering response to short days; medium plant height when grown as a pinched pot mum; recommended both as disbudded and spray pot mum; and spreading and prolific branching pattern.

3 Drawing Sheets

The present invention comprises a new and distinct cultivar of Chrysanthemum, botanically known as *Chrysanthemum morifolium,* Ramat., and referred to by the cultivar name Pomona.

Pomona, identified as 81893019, was originated from a cross made by Cornelis P. VandenBerg in a controlled breeding program in Salinas, Calif. in 1981.

The female parent of Pomona was the cultivar identified as Favor, disclosed in U.S. Plant Pat. No. 5,227. The male parent of Pomona was an unnamed seedling, identified as 78663011.

Pomona was discovered and selected as one flowering plant within the progeny of the stated cross by Cornelis P. VandenBerg in December of 1981, in a controlled environment in Salinas, Calif.

The first act of asexual reproduction of Pomona was accomplished when vegetative cuttings were taken from the initial selection in March of 1982 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Pomona are firmly fixed and are retained through successive generations of asexual reproduction.

Pomona has not been observed under all possible environmental conditions. The phenotype may vary significantly with variations in environment such as temperature, light intensity, and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Pomona, which, in combination, distinguish this Chrysanthemum as a new and distinct cultivar:

1. Flat capitulum form.
2. Decorative capitulum type.
3. Red-purple to purple ray floret color.
4. Diameter across face of capitulum up to 13.5 cm at maturity when grown as a pinched disbudded pot mum.

5. Uniform nine week photoperiodic flowering response to short days.
6. Medium plant height requiring 0 to 7 long days after pinch prior to short days and 1 application of 2500 ppm B-9 SP to attain a flowered plant height of 25 to 35 cm for year-round flowerings when grown as a pinched pot mum.
7. Recommended both as disbudded and spray pot mum.
8. Spreading and prolific branching pattern.

The accompanying photographic drawings show typical inflorescence and leaf characteristics of Pomona, with the colors being as nearly true as possible with illustrations of this type.

Sheet 1 is a color photograph of Pomona grown as a pinched disbudded pot mum.

Sheet 2 is a black and white photograph of three views of the inflorescence of Pomona.

Sheet 3 is a black and white photograph showing the upper and under sides of the leaves of Pomona at three stages of development (mature, intermediate and immature).

Of the commercial cultivars known to the inventor, the most similar in comparison to Pomona is the cultivar Luv, disclosed in U.S. Plant Pat. No. 4,960. Reference is made to attached Chart A, which compares certain characteristics of Pomona to the same characteristics of Luv.

Similar traits are capitulum type and form. The color of ray florets of Pomona is red-purple to purple, while the color of Luv is described as lavender. Pomona has a more spreading and prolific branching pattern, a larger diameter of capitulum, a larger plant height and a slower flowering response to short days when compared with Luv.

In the following description, color references are made to The Royal Horticultural Society Colour Chart. The color values were determined on plant material grown in Salinas, Calif. on June 15, 1987.

Classification:

*Botanical.*—*Chrysanthemum morifolium,* Ramat., cv. Pomona.

*Commercial.*—Decorative disbud and spray pot mum.

INFLORESCENCE

A. Capitulum:
*Form.*—Flat.
*Type.*—Decorative.
*Diameter across face.*—Up to 13.5 cm at maturity.

B. Corolla of ray florets:
*Color (general tonality from a distance of three meters).*—Red-purple.
*Color (upper surface).*—74C.
*Color (under surface).*—78C to 78D.
*Shape.*—Flat, oblong.

C. Corolla of disc florets:
*Color (mature).*—14B.
*Color (immature).*—144B.

D. Reproductive organs:
*Androecium.*—Present on disc florets only; scant pollen.
*Gynoecium.*—Present on both ray and disc florets.

PLANT

A. General appearance:
*Height.*—Medium; 25 to 35 cm as a pinched disbudded pot mum with 0 to 7 long days after pinch prior to short days and 1 application of 2500 ppm B-9 SP.

*Branching pattern.*—Spreading and prolific.

B. Foliage:
*Color (upper surface).*—147A.
*Color (under surface).*—147B.
*Shape.*—Lobed and slightly serrated.

CHART A

Comparison of Pomona and Luv

| Cultivar | Ray Floret Color | Capitulum Form and Type | Branching Pattern |
|---|---|---|---|
| Pomona | Red-purple to purple | Flat Decorative | Spreading and prolific |
| Luv | Lavender | Flat Decorative | Semi-spreading |

| Cultivar | Diameter across face of capitulum | Plant height | Flowering response period |
|---|---|---|---|
| Pomona | Up to 13.5 cm | Medium | 9 weeks |
| Luv | 105–115 mm | Short | 8 weeks |

Comparisons made of plants grown as pinched disbudded pot mums in Salinas, California

I claim:

1. A new and distinct cultivar of Chrysanthemum plant named Pomona, as illustrated and described, and parts thereof.

* * * * *

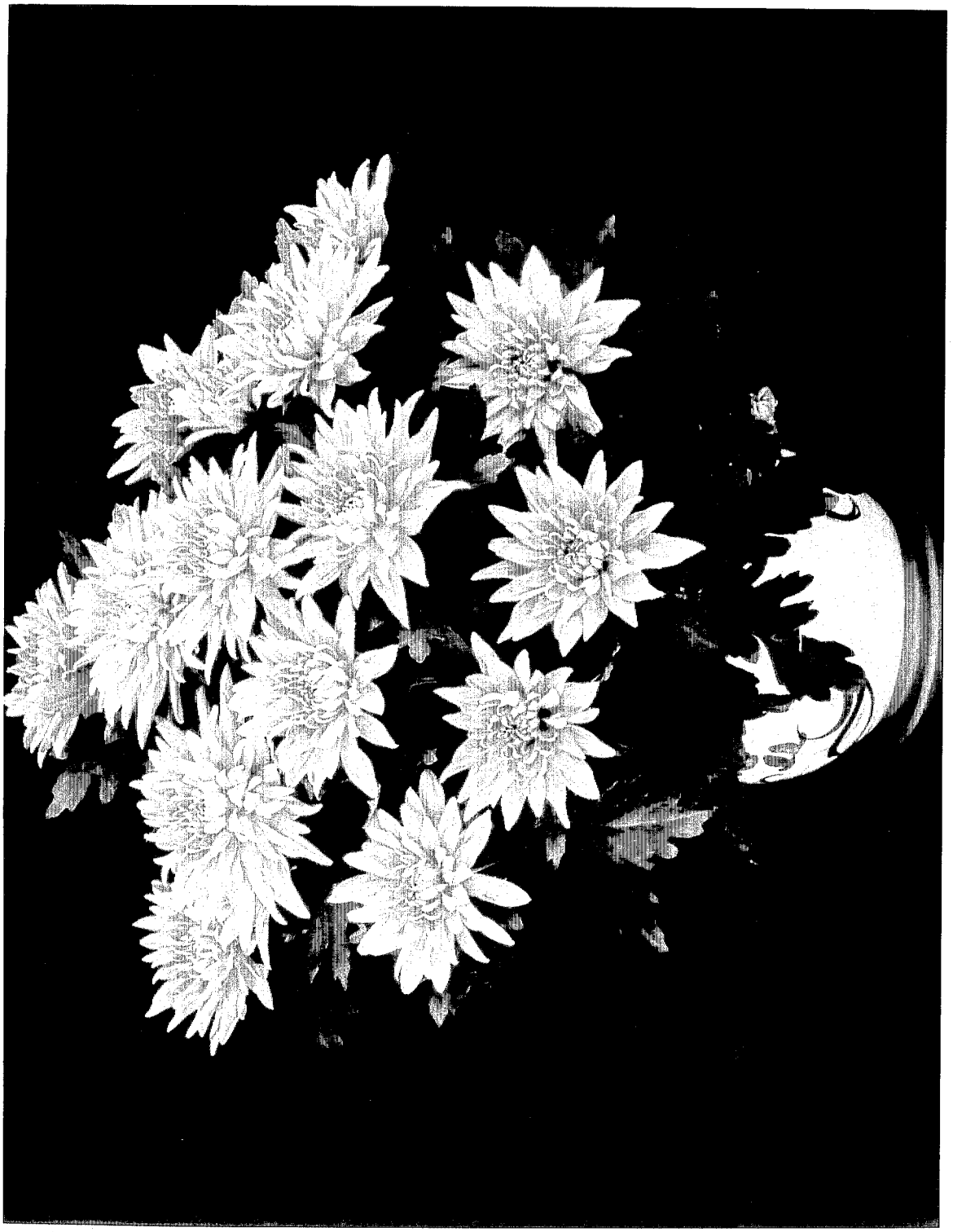

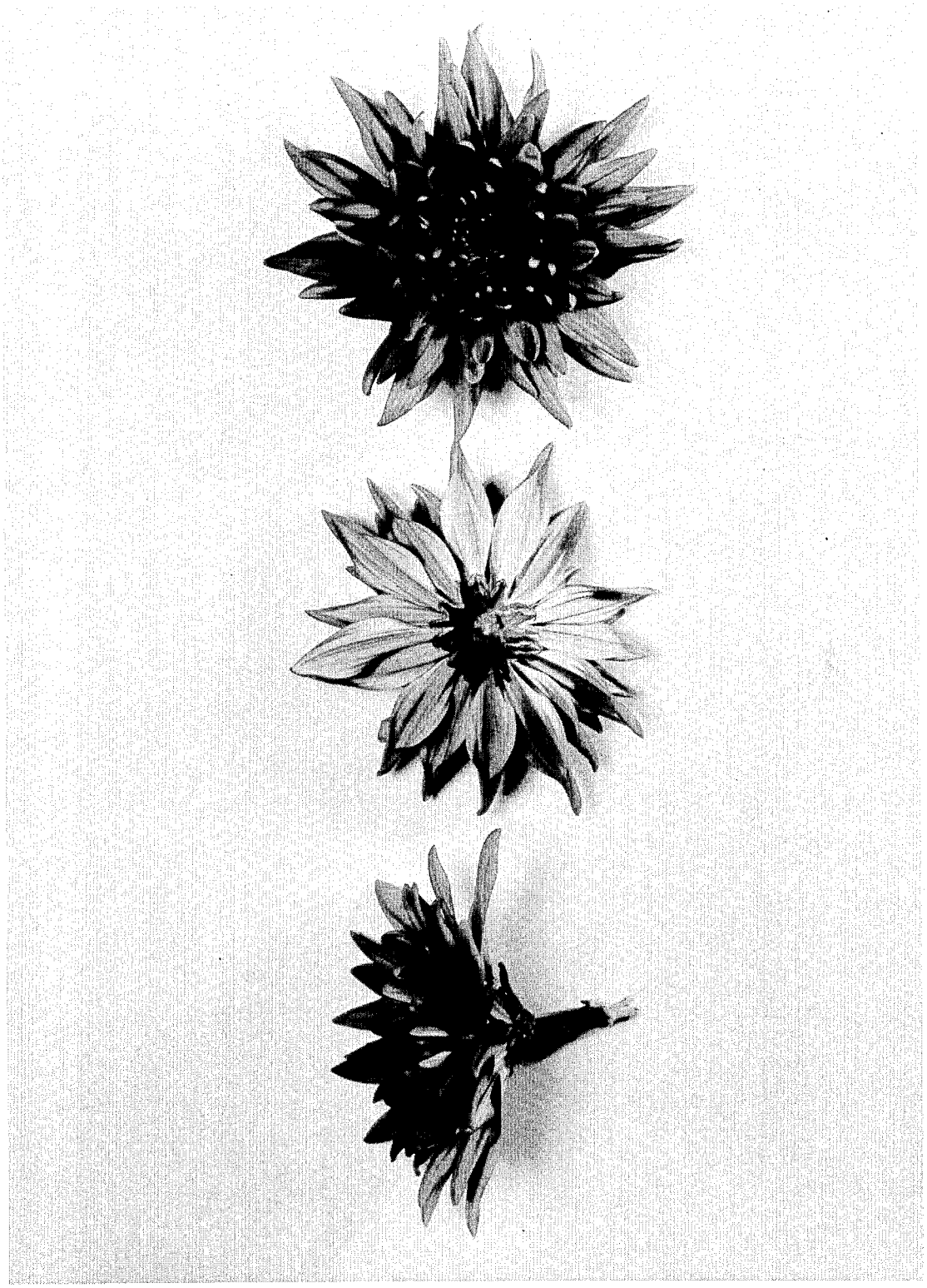

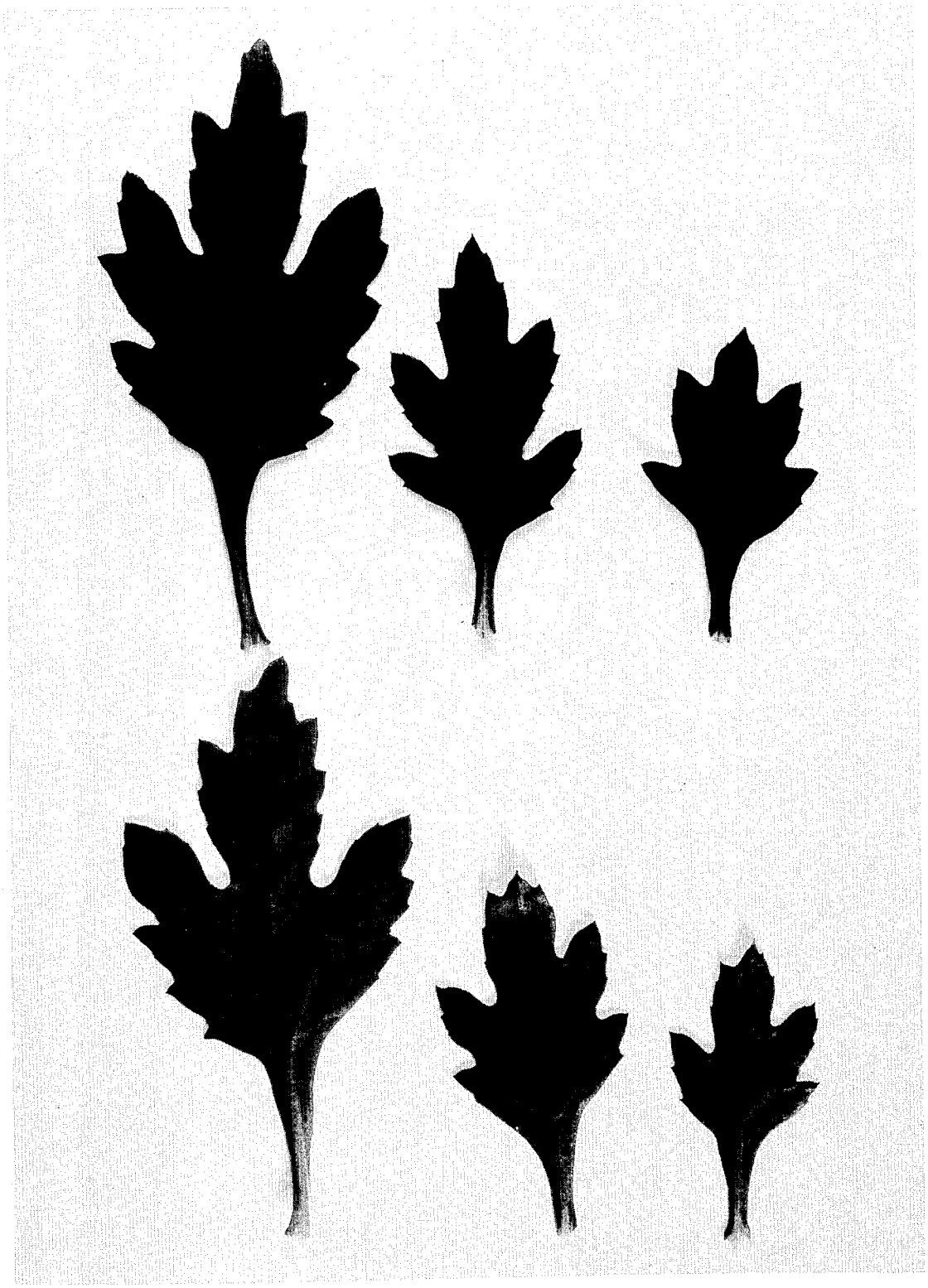

UNITED STATES PATENT AND TRADEMARK OFFICE

CERTIFICATE OF CORRECTION

PATENT NO. : Plant 6,802

DATED : May 16, 1989

INVENTOR(S) : Cornelis P. VandenBerg

It is certified that error appears in the above—identified patent and that said Letters Patent is hereby corrected as shown below:

Title page:

In the Abstract, line 3, the phrase "to purple" should be deleted.

Column 1, line 43, the phrase "to purple" should be deleted.

Column 2, line 30, the phrase "to purple" should be deleted.

Chart A, under the Heading Ray Floret Color, the phrase "to purple" should be deleted.

Signed and Sealed this

Twenty-third Day of April, 1991

*Attest:*

HARRY F. MANBECK, JR.

*Attesting Officer*

*Commissioner of Patents and Trademarks*